United States Patent
Nakagawa et al.

(10) Patent No.: US 9,910,084 B2
(45) Date of Patent: Mar. 6, 2018

(54) FLEXIBLE CIRCUIT BOARD INSPECTING APPARATUS

(71) Applicant: NIDEC-READ CORPORATION, Kyoto (JP)

(72) Inventors: Takashi Nakagawa, Kyoto (JP); Toshihide Matsukawa, Kyoto (JP); Osamu Hikita, Kyoto (JP); Michio Kaida, Kyoto (JP)

(73) Assignee: NIDEC-READ CORPORATION, Kyoto (JP)

(*) Notice: Subject to any disclaimer, the term of this patent is extended or adjusted under 35 U.S.C. 154(b) by 224 days.

(21) Appl. No.: 14/662,327

(22) Filed: Mar. 19, 2015

(65) Prior Publication Data

US 2015/0268298 A1    Sep. 24, 2015

(30) Foreign Application Priority Data

Mar. 20, 2014    (JP) ................................ 2014-058637

(51) Int. Cl.
  *G01R 31/28*    (2006.01)
  *G01R 31/308*   (2006.01)
  (Continued)

(52) U.S. Cl.
  CPC ..... *G01R 31/2808* (2013.01); *G01R 1/06794* (2013.01); *G01N 2021/95638* (2013.01);
  (Continued)

(58) Field of Classification Search
  CPC ............ G01R 31/2808; G01R 31/2806; G01R 31/2805; G01R 31/2801; G01R 1/07328;
  (Continued)

(56) References Cited

U.S. PATENT DOCUMENTS 4,829,241 A * 5/1989 Maelzer ............. G01R 1/07371
                                                              324/750.19
5,614,819 A * 3/1997 Nucci ................ G01R 1/07314
                                                              324/756.04
(Continued)

FOREIGN PATENT DOCUMENTS

JP    H10253688 A    9/1998
JP    H10332763 A    12/1998
(Continued)

OTHER PUBLICATIONS

Extended European Search Report issued in the corresponding European Application No. 151593191 dated Aug. 10, 2015, 11 pages.
(Continued)

*Primary Examiner* — Minh N Tang
(74) *Attorney, Agent, or Firm* — Viering, Jentschura & Partner mbB

(57) ABSTRACT

A flexible circuit board inspecting apparatus for conducting an inspection on a flexible circuit board includes a transport path and an inspection part mechanism. The transport path is configured to successively transport the flexible circuit board having a plurality of unit circuit boards arranged thereon. The inspection part mechanism is configured to bring and distance a jig for inspecting the flexible circuit board transported on the transport path close to and from the flexible circuit board. The transport path includes a longitudinal transport portion for transporting the flexible circuit board in a downward vertical direction. The inspection part mechanism moves the jig in a direction perpendicular to the flexible circuit board transported on the longitudinal transport portion to bring and distance the jig close to and from the flexible circuit board.

20 Claims, 6 Drawing Sheets

(51) Int. Cl.
*G01R 1/067* (2006.01)
*H05K 3/00* (2006.01)
*G01N 21/956* (2006.01)

(52) U.S. Cl.
CPC ........ *G01R 31/2805* (2013.01); *H05K 3/0008* (2013.01); *H05K 2203/1545* (2013.01); *H05K 2203/162* (2013.01)

(58) Field of Classification Search
CPC .. G01R 1/04; G01R 1/06772; G01R 1/07314; G01R 1/07335
See application file for complete search history.

(56) References Cited

U.S. PATENT DOCUMENTS

| | | | | |
|---|---|---|---|---|
| 6,118,292 | A * | 9/2000 | Antonello | G01R 31/2808 324/750.25 |
| 7,145,351 | B2 * | 12/2006 | Mizoguchi | G01R 31/2808 324/538 |
| 2004/0207423 | A1 | 10/2004 | Mizoguchi et al. | |
| 2006/0165274 | A1 | 7/2006 | Akiyama et al. | |
| 2009/0059195 | A1 | 3/2009 | Sato et al. | |

FOREIGN PATENT DOCUMENTS

| | | |
|---|---|---|
| JP | 2003121382 A | 4/2003 |
| JP | 2004228332 A | 8/2004 |
| JP | 2006071313 A | 3/2006 |
| JP | 2010149039 A | 7/2010 |
| JP | 5179289 B2 | 4/2013 |
| JP | 2013101017 A | 5/2013 |

OTHER PUBLICATIONS

Japanese Office Action based on Application No. 2014-058637 (4 Pages and 4 Pages of English translation) dated Oct. 19, 2017 (Reference Purpose Only).

* cited by examiner

FLEXIBLE CIRCUIT BOARD INSPECTING APPARATUS

CROSS REFERENCE TO RELATED APPLICATION

This application is based on and claims priority from Japanese Patent Application No. 2014-058637, filed on Mar. 20, 2014, the contents of which are hereby incorporated by reference in their entirety.

BACKGROUND

Technical Field

This disclosure relates to a flexible circuit board inspecting apparatus for inspecting a flexible circuit board.

Related Art

Heretofore, circuit board inspecting apparatuses have been proposed for inspecting a circuit pattern formed on a circuit board. Japanese Patent No. 5,179,289 discloses such a circuit board inspecting apparatus.

The circuit board inspecting apparatus disclosed in Japanese Patent No. 5,179,289 includes a circuit board fixing device for fixing a circuit board, and a probing device for probing the circuit board. The circuit board fixing device includes a clamp mechanism capable of clamping an edge of the circuit board. The probing device includes probe units each capable of bringing a probe pin into contact with a conductor pattern on the circuit board. The probe units are disposed in correspondence with front and back surfaces of the circuit board, respectively.

According to this configuration, the circuit board fixing device clamps the circuit board oriented horizontally, and the probe pins come into contact with both the surfaces of the circuit board from above and below, respectively. The probe units apply electric signals to the circuit board to conduct a predetermined electrical inspection on the circuit board.

The circuit board inspecting apparatus disclosed in Japanese Patent No. 5,179,289 is dedicated to the purpose of inspecting a so-called rigid circuit board which is a circuit board having a certain degree of hardness. Recently, on the other hand, circuit boards with flexibility (hereinafter, simply referred to as "flexible circuit boards") have been occasionally used for the purpose of reduction in thickness, improvement in electrical characteristic, and the like. For example, a large number of touch panels is collectively fabricated in the form of an elongated film-like multiple circuit board, and then a roll of the elongated film-like multiple circuit board is supplied to a subsequent process. Therefore, such a flexible circuit board brings about excellent advantages such as a cost reduction by mass production and an improved handleability.

This flexible circuit board brings about the advantages described above, but tends to be easily warped or bent. Therefore, this flexible circuit board is required to be handled with care. In this respect, the circuit board inspecting apparatus disclosed in Japanese Patent No. 5,179,289 is configured to inspect a circuit board by holding the circuit board from above and below with the probing device while clamping the circuit board oriented horizontally. Accordingly, if the circuit board inspecting apparatus disclosed in Japanese Patent No. 5,179,289 is used for inspecting the flexible circuit board, the flexible circuit board tends to be bowed downward under its own weight. Consequently, it is difficult to bring the probe pin into contact with an accurate position on the flexible circuit board. Particularly, it is considerably difficult to simultaneously inspect both surfaces of the flexible circuit board.

In the case where the circuit board inspecting apparatus disclosed in Japanese Patent No. 5,179,289 is used for inspecting the flexible circuit board, moreover, when the probe pin is brought into contact with the flexible circuit board from above, the flexible circuit board is applied with its own weight and a downward pressing force by the probe pin. Therefore, the flexible circuit board tends to be further bent. In order to prevent the flexible circuit board from being bent in such a case, a clamping device is employed for clamping the flexible circuit board more firmly. However, the use of the clamping device is not preferable since the clamping device increases in size, complexity, and weight.

In addition, the circuit board inspecting apparatus disclosed in Japanese Patent No. 5,179,289 moves the probe pin in an upward direction and a downward direction to bring and separate the probe pin into contact with and from the circuit board. Accordingly, the circuit board inspecting apparatus requires large drive means in order to lift up the heavy probe unit and a member for supporting the probe unit against gravity, so that this drive means causes an increase in cost.

SUMMARY

In view of the circumstances described above, an exemplary embodiment of the disclosure provides a flexible circuit board inspecting apparatus capable of smoothly conducting an inspection on a flexible circuit board and easily realizing a simplification and a weight reduction.

The technical challenges to be solved by the disclosure are as described above. Hereinafter, a description will be given of solutions to these technical challenges and the advantageous effects of the solutions.

An exemplary embodiment of the disclosure provides a flexible circuit board inspecting apparatus for conducting an inspection on a flexible circuit board. The flexible circuit board inspecting apparatus includes a transport path and an inspection part mechanism. The transport path is configured to successively transport the flexible circuit board having a plurality of unit circuit boards arranged thereon. The inspection part mechanism is configured to bring and distance an inspection part for inspecting the flexible circuit board transported on the transport path close to and from the flexible circuit board. The transport path includes a longitudinal transport portion for transporting the flexible circuit board in at least one of an upward vertical direction and a downward vertical direction. The inspection part mechanism moves the inspection part in a direction perpendicular to the flexible circuit board transported on the longitudinal transport portion to bring and distance the inspection part close to and from the flexible circuit board.

According to this configuration, the inspection part is brought close to and distanced from the longitudinal transport portion at which the straightness of the flexible circuit board is maintained. Thus, there is no necessity to take the warpage of the flexible circuit board under its own weight into consideration. Therefore, it is possible to inspect the flexible circuit board while accurately bringing the inspection part into alignment with the flexible circuit board. Accordingly, it is possible to easily omit or simplify a mechanism to clamp or guide the flexible circuit board. Therefore, it is possible to realize a cost reduction and a weight reduction of the flexible circuit board inspecting apparatus. Furthermore, for example, heat which is generated from a drive mechanism for moving the inspection part easily escapes in an upward direction and a downward direction at the longitudinal transport portion for the flexible circuit board. Thus, variations in temperature and humidity are less prone to occur. Accordingly, it is possible to inspect the flexible circuit board under a more stable environment.

Preferably, the flexible circuit board inspecting apparatus may be configured as follows. Specifically, the inspection part mechanism includes, as the inspection part, a jig having a plurality of probes brought into conductive contact with the flexible circuit board. The inspection part mechanism brings and separates the inspection part into contact with and from the flexible circuit board.

According to this configuration, it is possible to bring the jig into contact with the accurate position on the flexible circuit board by bringing and separating the jig into contact with and from the longitudinal transport portion at which the straightness of the flexible circuit board is maintained. As a result, it is possible to efficiently conduct an electrical inspection.

Preferably, the flexible circuit board inspecting apparatus may be configured as follows. Specifically, the jig includes a first jig brought into conductive contact with one surface of the flexible circuit board in a thickness direction of the flexible circuit board, and a second jig brought into conductive contact with the other surface of the flexible circuit board in the thickness direction. The flexible circuit board is subjected to the inspection in a state in which the flexible circuit board is sandwiched between the first jig and the second jig.

According to this configuration, each jig is brought into contact with the longitudinal transport portion at which the straightness of the flexible circuit board is maintained. Therefore, it is possible to conduct an electrical inspection while simultaneously bringing the two jigs into contact with the accurate positions on both the front and back surfaces of the flexible circuit board. Accordingly, it is possible to simultaneously inspect both the surfaces of the flexible circuit board. Therefore, it is possible to considerably improve the inspection efficiency.

Preferably, the flexible circuit board inspecting apparatus may be configured as follows. Specifically, the inspection part mechanism includes a first movement mechanism, a second movement mechanism, and an attitude change mechanism. The first movement mechanism is configured to move the jig within a plane parallel with the flexible circuit board. The second movement mechanism is configured to move the jig in parallel with the thickness direction of the flexible circuit board. The attitude change mechanism is configured to change the inclination of the jig within the plane parallel with the flexible circuit board.

According to this configuration, it is possible to bring and separate the jig into contact with and from the flexible circuit board while appropriately bringing the jig into alignment with the flexible circuit board. Therefore, it is possible to smoothly conduct an electrical inspection.

Preferably, the flexible circuit board inspecting apparatus may be configured as follows. Specifically, the inspection part mechanism includes, as the inspection part, an optical unit configured to measure an inspection area on the flexible circuit board. The inspection part mechanism brings and distances the inspection part close to and from the flexible circuit board to maintain an inspection length from the inspection part to the flexible circuit board.

According to this configuration, it is possible to appropriately control the length from the optical unit to the flexible circuit board. Therefore, it is possible to smoothly conduct an optical inspection.

Preferably, the flexible circuit board inspecting apparatus may be configured as follows. Specifically, the inspection part mechanism includes, as the inspection part, a first optical unit configured to measure an inspection area on one surface of the flexible circuit board in a thickness direction of the flexible circuit board, and a second optical unit configured to measure an inspection area on the other surface of the flexible circuit board in the thickness direction. The first optical unit and the second optical unit are disposed at different heights from each other.

According to this configuration, it is possible to simultaneously inspect both the front and back surfaces of the flexible circuit board. Therefore, it is possible to improve the efficiency of an optical inspection. Moreover, the two optical units are disposed at different heights from each other. Therefore, it is possible to realize such a layout that the two optical units are less prone to have a mutual influence upon measurement of the inspection areas.

Preferably, the flexible circuit board inspecting apparatus may be configured as follows. Specifically, the inspection part mechanism includes an image capturing part configured to capture an image of the flexible circuit board. The inspection part mechanism brings the inspection part into alignment with the flexible circuit board, based on captured image information obtained by capturing the image of the flexible circuit board by the image capturing part.

According to this configuration, it is possible to bring the inspection part into alignment with the flexible circuit board with high accuracy, based on the information obtained by actually capturing the image of the flexible circuit board.

Preferably, the flexible circuit board inspecting apparatus may be configured as follows. Specifically, the inspection part mechanism includes a first inspection part, a second inspection part, a first image capturing part, and a second image capturing part. The first inspection part is disposed at one side of the flexible circuit board transported on the longitudinal transport portion, in a thickness direction of the flexible circuit board. The second inspection part is disposed at the other side of the flexible circuit board in the thickness direction. The first image capturing part is disposed at one side of the flexible circuit board in the thickness direction. The second image capturing part is disposed at the other side of the flexible circuit board in the thickness direction. The first image capturing part captures an image of the second inspection part. The second image capturing part captures an image of the first inspection part.

According to this configuration, the image capturing part captures the image of the inspection part disposed at the opposite side to the image capturing part in the thickness direction of the flexible circuit board with the flexible circuit board interposed between the image capturing part and the inspection part. Thus, it is possible to obtain useful information concerning a positional relation, a surface state, and the like of the inspection part.

Preferably, the flexible circuit board inspecting apparatus may further include a supply part configured to set thereon a circuit board roll from which the flexible circuit board is successively supplied.

According to this configuration, it is possible to successively supply the flexible circuit board from the circuit board roll and to successively inspect the large number of unit circuit boards. Therefore, it is possible to improve the inspection efficiency.

Preferably, the flexible circuit board inspecting apparatus may further include a foreign matter recovery part configured to recover a foreign matter and disposed at a height lower than a height of the inspection part.

According to this configuration, even in a case where a foreign matter such as a particle is generated, for example, upon movement of the inspection part, the foreign matter recovery part can efficiently recover the foreign matter falling under its own weight. Therefore, it is possible to avoid degradation in quality of the flexible circuit board due to the adhesion of the foreign matter.

Preferably, the flexible circuit board inspecting apparatus may further include a suction guide configured to suck the flexible circuit board by negative pressure and disposed on the longitudinal transport portion.

According to this configuration, the suction guide can fixedly hold the flexible circuit board oriented in the vertical direction. Therefore, it is possible to smoothly conduct an inspection using the inspection part mechanism. Moreover, it is possible to easily switch between the hold and release of the flexible circuit board by switching between the start and stop of the supply of the negative pressure to the suction guide.

The foregoing and other objects, features, aspects, and advantages of the disclosed invention will become more apparent from the following detailed description, when taken in conjunction with the accompanying drawings.

DETAILED DESCRIPTION

Figure 1:
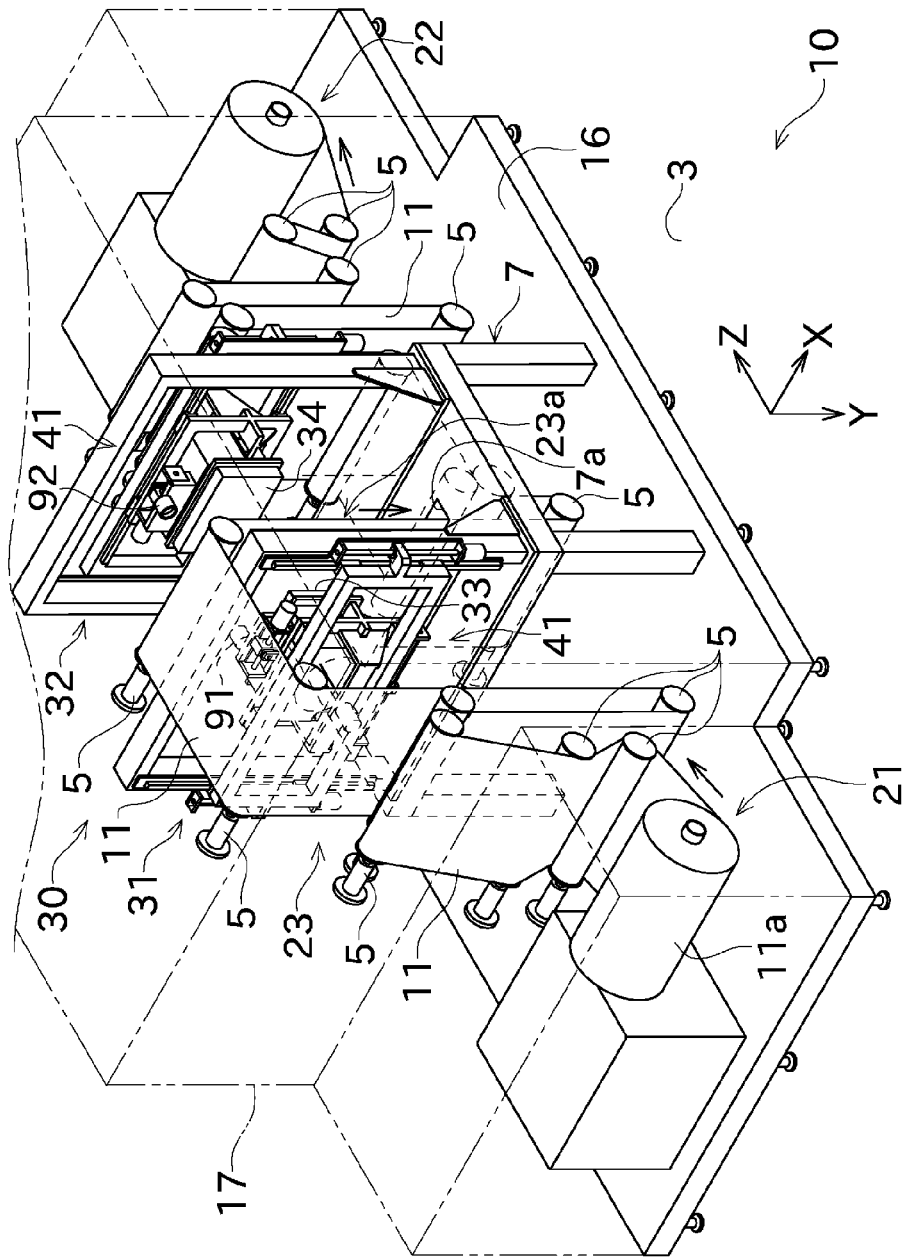
FIG. 1 is a schematic perspective view illustrating an overall configuration of a flexible circuit board inspecting apparatus according to a first embodiment.
Figure 2:
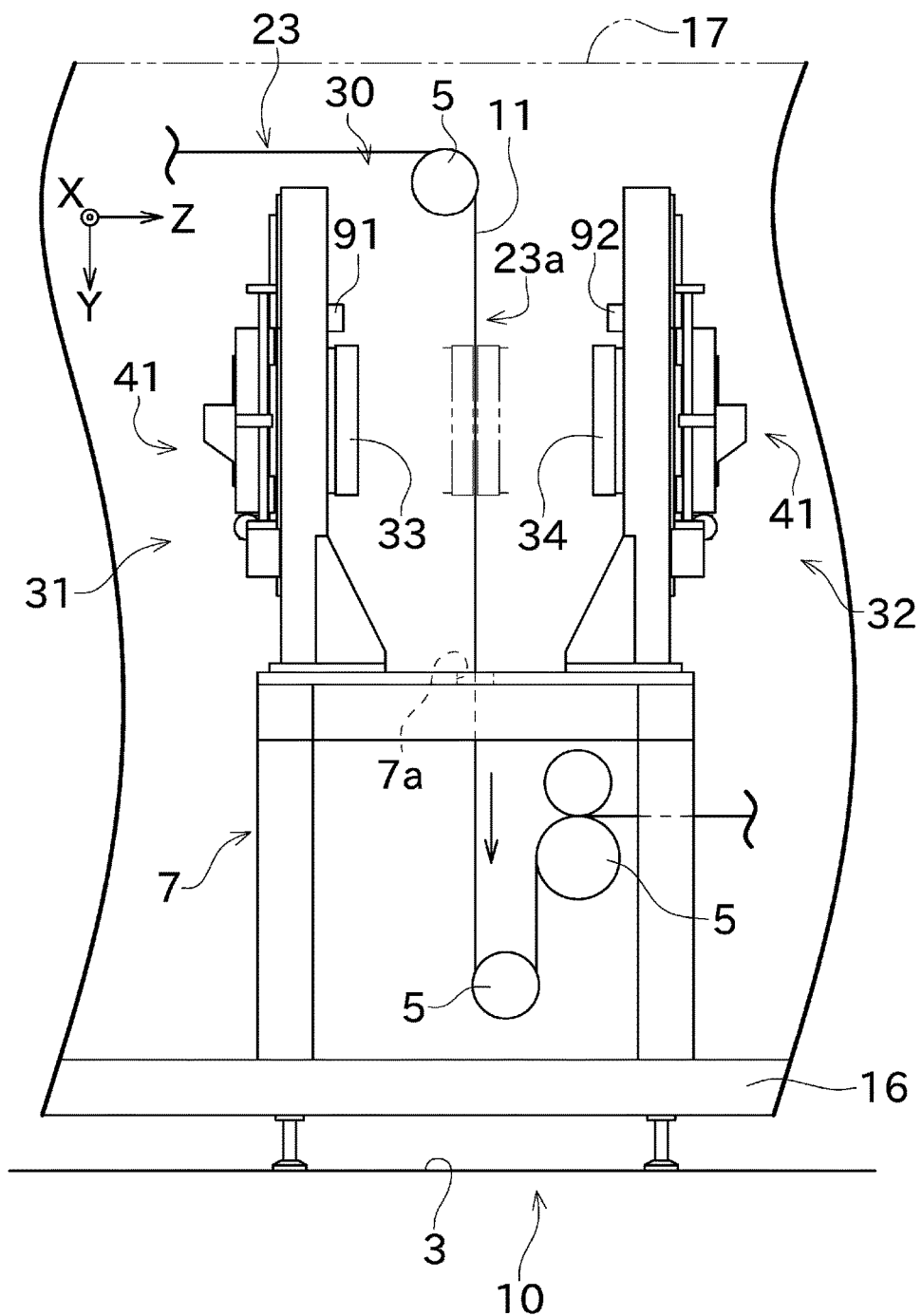
FIG. 2 is a front view illustrating a configuration around a longitudinal transport portion for a flexible circuit board.
Figure 3:
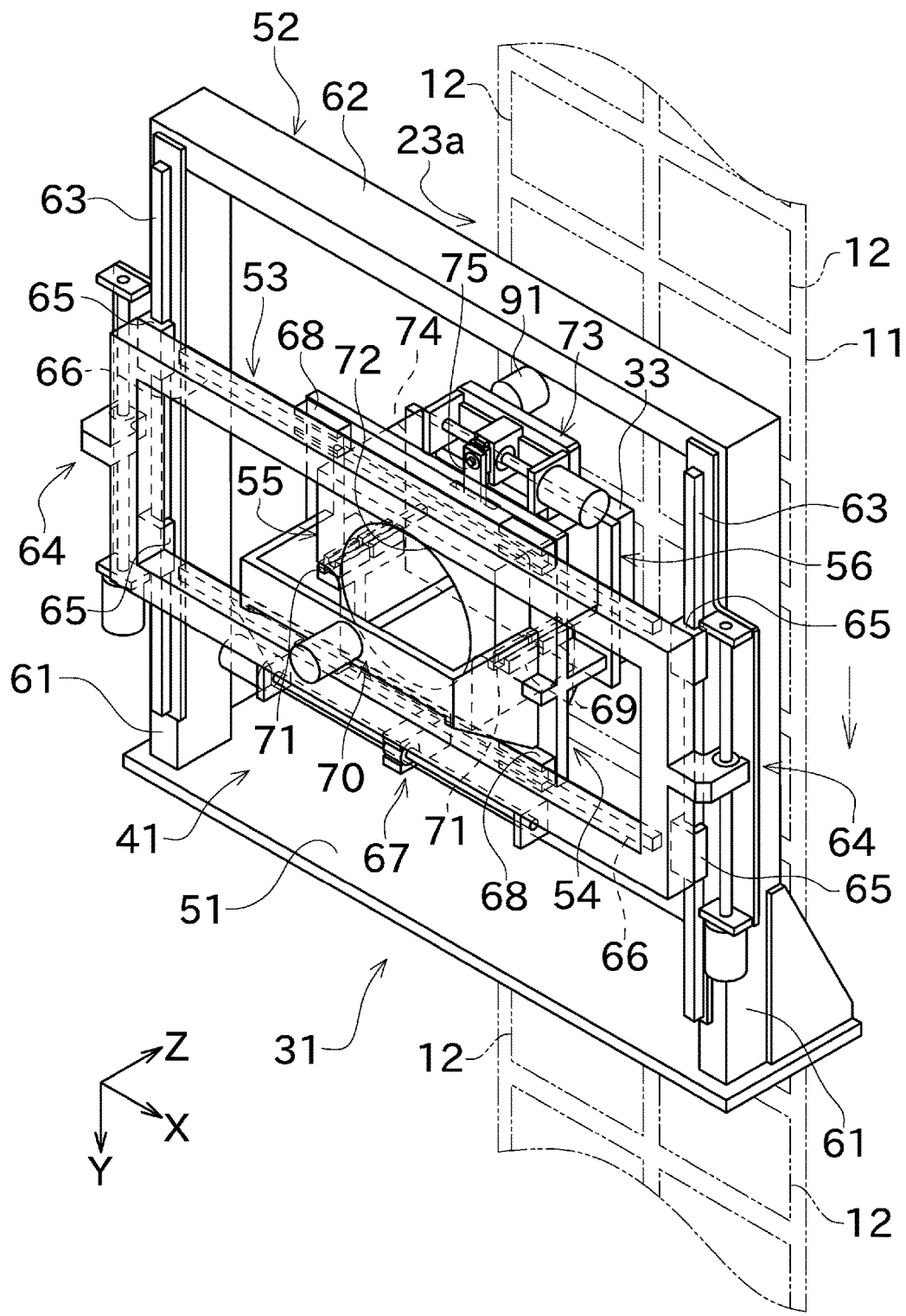
FIG. 3 is a perspective view illustrating a specific configuration of a jig mechanism.

Various embodiments of the disclosure will be described below with reference to the drawings. FIG. 1 is a schematic perspective view illustrating an overall configuration of a flexible circuit board inspecting apparatus 10 according to a first embodiment. FIG. 2 is a front view illustrating a configuration around a longitudinal transport portion 23a for a flexible circuit board 11. FIG. 3 is a perspective view illustrating a specific configuration of a first jig mechanism 31.

The flexible circuit board inspecting apparatus 10 according to the first embodiment illustrated in FIG. 1 is configured to set thereon the flexible circuit board 11 to be inspected, and to conduct an electrical inspection on a circuit pattern formed on the flexible circuit board 11. Specific examples of the electrical inspection include an inspection as to continuity or a short-circuit in a circuit pattern, an inspection as to a capacitance of a circuit pattern, and the like. The flexible circuit board inspecting apparatus 10 conducts these inspections as required, thereby determining whether or not the circuit pattern is acceptable.

In the first embodiment, the flexible circuit board 11 is formed into an elongated thin sheet shape (i.e., a film shape). The flexible circuit board 11 corresponds to a so-called multiple circuit board having a large number of unit circuit boards arranged thereon. At least some of these unit circuit boards are identical in configuration with one another.

The flexible circuit board 11 may be any kinds of circuit boards with flexibility. In the first embodiment, examples of the flexible circuit board 11 may include, but not limited thereto, a flexible transparent touch panel film having a large number of transparent touch panel circuit boards arranged thereon as unit circuit boards.

The flexible circuit board inspecting apparatus 10 includes a base member 16 mounted on a horizontal installation surface 3, and an accommodation chamber 17 disposed on the base member 16. The flexible circuit board inspecting apparatus 10 also includes a feed part (a supply part) 21, a reel part 22, a transport path 23, and an inspection part mechanism 30 each accommodated in the accommodation chamber 17.

The feed part 21 is configured to set thereon a roll of the flexible circuit board 11 (i.e., a circuit board roll 11a). In the flexible circuit board inspecting apparatus 10, the feed part 21 successively feeds the flexible circuit board 11 from the circuit board roll 11a to the reel part 22 via the transport path 23. The reel part 22 includes an electric motor (not illustrated) driven for reeling the flexible circuit board 11. The electric motor is intermittently driven to repeat the transport of the flexible circuit board 11 and a halt on the transport in order that the inspection part mechanism 30 inspects the flexible circuit board 11. The electric motor for the transport may be provided on a guide roller 5 (to be described later) which is disposed at some midpoint in the transport path 23.

The flexible circuit board inspecting apparatus 10 includes a plurality of guide rollers 5 for guiding the flexible circuit board 11 along the transport path 23. A layout of the guide rollers 5 forms the longitudinal transport portion 23a at some midpoint in the transport path 23 (i.e., at a center portion of the flexible circuit board inspecting apparatus 10) so as to transport the flexible circuit board 11 downward (see FIGS. 1 and 2). In the longitudinal transport portion 23a, a direction of transporting the flexible circuit board 11 corresponds to a vertical direction, but can also be said as a direction perpendicular to the installation surface 3 or a direction along gravity.

Herein, a plane parallel with the flexible circuit board 11 transported on the longitudinal transport portion 23a is occasionally referred to as an X-Y plane, and a direction perpendicular to the X-Y plane is occasionally referred to as a Z direction. The X-Y plane corresponds to a plane parallel with the vertical direction, and the Z direction is oriented horizontally.

The flexible circuit board inspecting apparatus 10 includes a horizontal inspection table 7. The inspection table 7 has a through hole 7a formed at a center of a top portion thereof, and the flexible circuit board 11 on the longitudinal transport portion 23a passes through the through hole 7a.

The inspection part mechanism 30 is disposed on the inspection table 7. The inspection part mechanism 30 includes a first jig mechanism 31 and a second jig mechanism 32. The two jig mechanisms 31 and 32 are disposed with the flexible circuit board 11 on the longitudinal transport portion 23a sandwiched therebetween. Moreover, the first jig mechanism 31 and the second jig mechanism 32 are disposed to face each other.

The first jig mechanism 31 includes a first jig (a first inspection part, an inspection part) 33 which can be brought into contact with and separated from the flexible circuit board 11. The second jig mechanism 32 includes a second jig (a second inspection part, an inspection part) 34 which can be brought into contact with and separated from the flexible circuit board 11. The first jig 33 is disposed at one side of the flexible circuit board 11 in a thickness direction of the flexible circuit board 11, and the second jig 34 is disposed at the other side of the flexible circuit board 11 in the thickness direction. Moreover, the first jig 33 and the second jig 34 are disposed to face each other.

The first jig mechanism 31 includes a first camera (a first image capturing part) 91 capable of capturing an image of the flexible circuit board 11. The second jig mechanism 32 includes a second camera (a second image capturing part) 92 capable of capturing an image of the flexible circuit board 11. The first camera 91 is disposed at one side of the flexible circuit board 11 in the thickness direction of the flexible circuit board 11, and the second camera 92 is disposed at the other side of the flexible circuit board 11 in the thickness direction. Moreover, the first camera 91 is disposed to face the second jig mechanism 32, and the second camera 92 is disposed to face the first jig mechanism 31. Accordingly, in a case where the flexible circuit board 11 is not transported on the longitudinal transport portion 23a, the first camera 91 is capable of capturing an image of the second jig 34, and the second camera 92 is capable of capturing an image of the first jig 33. Also in a case where the flexible circuit board 11 is transported on the longitudinal transport portion 23a, the cameras 91 and 92 are capable of capturing images of the opposite jigs 34 and 33 disposed at the opposite sides to the cameras 91 and 92 with the flexible circuit board 11 interposed between the cameras 91, 92 and the jigs 34, 33 as long as the flexible circuit board 11 is transparent as described in the first embodiment. Thus, it is possible to obtain information useful for positioning and maintenance, such as the positions or surface states of the opposite jigs 33 and 34.

In the first embodiment, although not limited thereto, the two cameras 91 and 92 are disposed above the jigs 33 and 34, respectively. For example, the first camera 91 may be disposed above the first jig 33 whereas the second camera 92 may be disposed below the second jig 34.

The first jig mechanism 31 includes a movement mechanism 41 for moving the first jig 33. The movement mechanism 41 includes an X-Y movement mechanism that allows the first jig 33 to move within the plane parallel with the flexible circuit board 11 on the longitudinal transport portion 23a (i.e., the X-Y plane). The movement mechanism 41 also includes a Z movement mechanism that allows the first jig 33 to move in the Z direction, that is, the horizontal direction. Thus, the movement mechanism 41 brings the first jig 33 close to the flexible circuit board 11, thereby bringing the first jig 33 into contact with the flexible circuit board 11. Alternatively, the movement mechanism 41 cancels this contact (i.e., separates the first jig 33 from the flexible circuit board 11), thereby distancing the first jig 33 from the flexible circuit board 11. The movement mechanism 41 also includes an attitude change mechanism capable of changing the inclination of the first jig 33 within the plane parallel with the flexible circuit board 11.

The second jig mechanism 32 is similar in configuration to the first jig mechanism 31, and includes a movement mechanism 41. The movement mechanism 41 includes an X-Y movement mechanism that allows the second jig 34 to move within the plane parallel with the flexible circuit board 11 on the longitudinal transport portion 23a (i.e., the X-Y plane). The movement mechanism 41 also includes a Z movement mechanism that allows the second jig 34 to move in the Z direction, that is, the horizontal direction. Thus, the movement mechanism 41 brings the second jig 34 close to the flexible circuit board 11, thereby bringing the second jig 34 into contact with the flexible circuit board 11. Alternatively, the movement mechanism 41 cancels the contact (i.e., separates the second jig 34 from the flexible circuit board 11), thereby distancing the second jig 34 from the flexible circuit board 11. The movement mechanism 41 also includes an attitude change mechanism capable of changing the inclination of the second jig 34 within the plane parallel with the flexible circuit board 11.

The specific configurations of the movement mechanisms 41 and 41 in the two jig mechanisms 31 and 32 will be described later.

The flexible circuit board inspecting apparatus 10 configured as described above moves the first jig 33 and second jig 34 of the inspection part mechanism 30 with respect to the flexible circuit board 11 transported on the longitudinal transport portion 23a. Thus, the flexible circuit board inspecting apparatus 10 is capable of bringing the two jigs 33 and 34 into contact with the flexible circuit board 11 such that the two jigs 33 and 34 simultaneously hold the flexible circuit board 11 in the thickness direction of the flexible circuit board 11. Alternatively, the flexible circuit board inspecting apparatus 10 is capable of canceling the contact (i.e., separating the two jigs 33 and 34 from the flexible circuit board 11). In other words, the flexible circuit board inspecting apparatus 10 is capable of bringing and separating the jigs 33 and 34 into contact with and from an inspection point defined on the circuit pattern of the flexible circuit board 11.

Each of the first jig 33 and the second jig 34 is simply depicted in the drawings. Actually, each of the first jig 33 and the second jig 34 is formed of a member having a large number of electrically conductive needle-shaped members (probes) or an electrically conductive rubber member exhibiting electric conductivity in a pressed state. The probe of the first jig 33 can be brought into conductive contact with a predetermined inspection point defined on one surface (a first surface) of the flexible circuit board 11 in the thickness direction of the flexible circuit board 11. The probe of the second jig 34 can be brought into conductive contact with a predetermined inspection point defined on the other surface (a second surface) of the flexible circuit board 11 in the thickness direction. Herein, the state in which the probes of the jigs 33 and 34 are brought into conductive contact with the flexible circuit board 11 is occasionally represented as "the jigs 33 and 34 are brought into conductive contact with the flexible circuit board 11".

In the first embodiment, each of the first jig 33 and the second jig 34 is configured to come into contact with an inspection point on a circuit pattern for each unit circuit board. In place of this configuration, each of the first jig 33 and the second jig 34 may be configured to transmit and receive electric signals by capacitive coupling to a predetermined inspection point.

The probes of the first jig 33 and second jig 34 are connected to a current supply part (not illustrated) and a current measurement part (not illustrated) of the flexible circuit board inspecting apparatus 10, thereby conducting an electrical inspection on the flexible circuit board 11. Specifically, the flexible circuit board inspecting apparatus 10 supplies a current to the circuit pattern of the flexible circuit board 11 in the state in which the two jigs 33 and 34 are in contact with the inspection points on the flexible circuit board 11, and then measures the magnitude of the current flowing through the flexible circuit board 11. The flexible circuit board inspecting apparatus 10 also includes a voltage measurement part (not illustrated) capable of measuring a potential difference generated upon supply of the current to the circuit pattern. In the case where the jigs 33 and 34 are capacitively coupled to the circuit pattern of the flexible circuit board 11, moreover, the flexible circuit board inspecting apparatus 10 measures the electrostatic capacitance of each jig, thereby calculating the potential difference.

With reference to FIG. 3, next, a specific description will be given of the two jig mechanisms 31 and 32 of the inspection part mechanism 30. Herein, the first jig mechanism 31 and the second jig mechanism 32 are substantially identical in configuration with each other; therefore, the configuration of the first jig mechanism 31 is representatively described below. FIG. 3 does not illustrate the inspection table 7 and the second jig mechanism 32 for simplification of the illustration.

The first jig mechanism 31 includes a bottom plate 51, a fixed frame 52, a first movable frame 53, a second movable frame 54, an advancement and retreat member 55, and a rotary member 56.

The bottom plate 51 is disposed on a lower portion of the first jig mechanism 31, and is formed of a flat plate-shaped member. The bottom plate 51 can be fixed to an upper surface of the inspection table 7 described above.

The fixed frame 52 is formed of a gate-shaped member, and is fixed upright on an upper surface of the bottom plate 51. The fixed frame 52 includes a pair of longitudinal members 61 and 61, and a lateral member 62 disposed to couple upper ends of the longitudinal members 61 and 61 to each other. The longitudinal members 61 and 61 have longitudinal guide rails 63 and 63 fixed thereto. The longitudinal members 61 and 61 also have longitudinal feed mechanisms 64 and 64 attached thereto. Each of the longitudinal feed mechanisms 64 and 64 includes an electric motor and a screw feed mechanism.

The first movable frame 53 is formed of a rectangular frame-shaped member, and is supported by the fixed frame 52. Specifically, the first movable frame 53 has longitudinal sliders 65 and 65 attached thereto. The longitudinal sliders 65 and 65 are movable along the longitudinal guide rails 63 and 63 fixed to the fixed frame 52. Moreover, the first movable frame 53 is coupled to the longitudinal feed mechanisms 64 and 64 attached to the fixed frame 52. According to this configuration, the electric motors of the longitudinal feed mechanisms 64 and 64 are driven to allow the first movable frame 53 to move in a lengthwise direction (a Y direction) of the flexible circuit board 11 on the longitudinal transport portion 23a.

The first movable frame 53 has a lateral guide rail 66 fixed thereto. The first movable frame 53 also has a lateral feed mechanism 67 attached thereto. The lateral feed mechanism 67 includes an electric motor and a screw feed mechanism.

The second movable frame 54 is formed of a frame-shaped member, and is supported by the first movable frame 53. Specifically, the second movable frame 54 has a lateral slider 68 attached thereto. The lateral slider 68 is movable along the lateral guide rail 66 fixed to the first movable frame 53. Moreover, the second movable frame 54 is coupled to the lateral feed mechanism 67 attached to the first movable frame 53. According to this configuration, the electric motor of the lateral feed mechanism 67 is driven to allow the second movable frame 54 to move in a widthwise direction (an X direction) of the flexible circuit board 11 on the longitudinal transport portion 23a.

The second movable frame 54 has advancement and retreat sliders 69 and 69 fixed thereto. The second movable frame 54 also has an advancement and retreat mechanism 70 attached thereto. The advancement and retreat mechanism 70 includes an electric motor and a screw feed mechanism.

The advancement and retreat member 55 is formed of a block-shaped member, and is supported by the second movable frame 54. Specifically, the advancement and retreat member 55 has advancement and retreat guide rails 71 and 71 attached thereto. The advancement and retreat sliders 69 and 69 fixed to the second movable frame 54 are movable along the advancement and retreat guide rails 71 and 71. Moreover, the advancement and retreat member 55 is coupled to the advancement and retreat mechanism 70 attached to the second movable frame 54. According to this configuration, the electric motor of the advancement and retreat mechanism 70 is driven to allow the advancement and retreat member 55 to move in the thickness direction of the flexible circuit board 11 on the longitudinal transport portion 23a (i.e., in the direction so as to be brought into close to and distanced from the flexible circuit board 11, the Z direction).

The advancement and retreat member 55 has a round hole 72 formed therein, and a bearing (not illustrated) is attached to the round hole 72. The advancement and retreat member 55 also has a rotary mechanism 73 attached thereto. The rotary mechanism 73 includes an electric motor and a screw feed mechanism.

The rotary member 56 includes a cylindrical shaft (not illustrated), and a mounting plate 74 fixed to the shaft. The shaft is inserted into the round hole 72 formed in the advancement and retreat member 55, and is rotatably supported by the bearing. The first jig 33 is detachably fixed to the mounting plate 74.

The shaft of the rotary member 56 is coupled to the rotary mechanism 73 attached to the advancement and retreat member 55, via an arm 75 inserted into a hole formed in the advancement and retreat member 55. According to this configuration, the electric motor of the rotary mechanism 73 is driven to rotate the rotary member 56 and to allow the mounting plate 74 (and the first jig 33 fixed to the mounting plate 74) to rotate within the X-Y plane.

In the first jig mechanism 31 configured as described above, a combination of the longitudinal feed mechanism 64 with the lateral feed mechanism 67 is equivalent to the X-Y movement mechanism. Moreover, the advancement and retreat mechanism 70 is equivalent to the Z movement mechanism. Further, the rotary mechanism 73 is equivalent to the attitude change mechanism. The X-Y movement mechanism, the Z movement mechanism, and the attitude change mechanism form the movement mechanism 41. The first jig mechanism 31 includes the first camera 91 and analyzes an image (captured image information) of the flexible circuit board 11 captured by the first camera 91, thereby detecting a position of a positioning mark (a fiducial mark) (not illustrated) on the flexible circuit board 11. The flexible circuit board inspecting apparatus 10 also includes a controller (a control part) (not illustrated) for controlling the movement mechanism 41. The flexible circuit board inspecting apparatus 10 brings the first jig 33 into contact with the unit circuit board 12 of the flexible circuit board 11 while appropriately adjusting the position and attitude of the first jig 33 within the X-Y plane in accordance with the detected position of the fiducial mark. Thus, the flexible circuit board inspecting apparatus 10 is capable of smoothly conducting an electrical inspection by bringing the first jig 33 into contact with the unit circuit board 12 of the flexible circuit board 11 (probing the unit circuit board 12 of the flexible circuit board 11 with the first jig 33) while accurately bringing the first jig 33 into alignment with the unit circuit board 12 of the flexible circuit board 11. The foregoing description of the first jig mechanism 31 may hold true for the second jig mechanism 32.

The first jig mechanism 31 and the second jig mechanism 32 conduct an electrical inspection by moving the first jig 33 and the second jig 34 in the horizontal direction so as to bring the first jig 33 and the second jig 34 into contact with the flexible circuit board 11 transported in an upward direction and a downward direction on the longitudinal transport portion 23a. The flexible circuit board 11 may be bent (warped) under its own weight at the portion where the flexible circuit board 11 is transported horizontally between the guide roller 5 and the guide roller 5. On the other hand, the straightness of the flexible circuit board 11 can be favorably maintained at the longitudinal transport portion 23a. According to the first embodiment, thus, it is possible to bring the jigs 33 and 34 of the jig mechanisms 31 and 32 into contact with the flexible circuit board 11 kept tight under its own weight, without using a special clamp mechanism or guide mechanism. Therefore, it is possible to enhance the accuracy to bring the jigs 33 and 34 into contact with the flexible circuit board 11, with a simple configuration. Accordingly, it is possible to conduct, without any problems, an inspection in such a manner that the first jig 33 is brought into contact with an accurate position on one surface of the flexible circuit board 11 in the thickness direction of the flexible circuit board 11, the second jig 34 is brought into contact with an accurate position on the other surface of the flexible circuit board 11 in the thickness direction, and electric signals are inputted to and outputted from both the front and back surfaces of the flexible circuit board 11, as described in the first embodiment.

Moreover, the electric motors of the longitudinal feed mechanism 64, lateral feed mechanism 67, advancement and retreat mechanism 70, and rotary mechanism 73 are driven to generate heat. Each of these electric motors is disposed in the vicinity of the longitudinal transport portion 23a. Therefore, the generated heat can easily escape in the upward direction and the downward direction (alternatively, an air flow substantially flowing in the upward direction and the downward direction along the flexible circuit board 11 on the longitudinal transport portion 23a may be positively generated in the accommodation chamber 17). As a result, it is possible to stabilize a temperature or a humidity around the portion where the jigs 33 and 34 are brought into contact with the flexible circuit board 11, which leads to the favorable stability of an inspection environment.

Further, the jigs 33 and 34 are driven in the horizontal direction by the electric motor of the advancement and retreat mechanism 70, and are brought into contact with and separated from the flexible circuit board 11. Accordingly, it is possible to move the jig 33 (34) in the Z direction in a state in which the fixed frame 52 (the longitudinal feed mechanism 64) bears the weight of the jig 33 (34) as well as the weights of the first movable frame 53, second movable frame 54, advancement and retreat member 55, and rotary member 56 each supporting the jig 33 (34). Accordingly, the electric motor of the advancement and retreat mechanism 70 does not need to bear the heavy weight. Therefore, it is possible to realize a simplification, a size reduction, and the like of the electric motor. Moreover, it is possible to suppress the load on the electric motor of the advancement and retreat mechanism 70 as described above. As a result, it is possible to quickly accelerate and halt the electric motor in order to bring and separate the jig 33 (34) into contact with and from the flexible circuit board 11, which leads to improved inspection efficiency.

As described above, the flexible circuit board inspecting apparatus 10 according to the first embodiment is configured to conduct an inspection on the flexible circuit board 11. The flexible circuit board inspecting apparatus 10 includes the transport path 23 and the inspection part mechanism 30. The transport path 23 is configured to successively transport the flexible circuit board 11 having the plurality of unit circuit boards 12 arranged thereon. The inspection part mechanism 30 allows the first jig 33 and second jig 34 for inspecting the flexible circuit board 11 transported on the transport path 23 to be brought close to and distanced from the flexible circuit board 11. The transport path 23 includes the longitudinal transport portion 23a for transporting the flexible circuit board 11 in the downward vertical direction. The inspection part mechanism 30 moves the first jig 33 and the second jig 34 in the direction perpendicular to the flexible circuit board 11 transported on the longitudinal transport portion 23a to bring and distance the first jig 33 and the second jig 34 close to and from the flexible circuit board 11.

According to this configuration, each of the first jig 33 and the second jig 34 is brought close to and distanced from the longitudinal transport portion 23a at which the straightness of the flexible circuit board 11 is maintained. Thus, there is no necessity to take the warpage of the flexible circuit board 11 under its own weight into consideration. Therefore, it is possible to conduct an electrical inspection on the flexible circuit board 11 while easily bringing each of the first jig 33 and the second jig 34 into contact with the accurate position on the flexible circuit board 11. Accordingly, it is possible to easily omit or simplify a mechanism to clamp or guide the flexible circuit board 11. Therefore, it is possible to realize a cost reduction and a weight reduction of the flexible circuit board inspecting apparatus 10. Furthermore, for example, heat which is generated from a drive mechanism for moving the first jig 33 or the second jig 34 easily escapes in the upward direction and the downward direction at the longitudinal transport portion 23a for the flexible circuit board 11. Thus, variations in temperature and humidity are less prone to occur. Accordingly, it is possible to inspect the flexible circuit board 11 under a more stable environment.

In the flexible circuit board inspecting apparatus 10 according to the first embodiment, the inspection part mechanism 30 includes, as an inspection part, the jigs 33 and 34 each having the plurality of probes brought into conductive contact with the flexible circuit board 11. The inspection part mechanism 30 brings and separates the two jigs 33 and 34 into contact with and from the flexible circuit board 11.

According to this configuration, it is possible to efficiently conduct an electrical inspection by use of the plurality of jigs 33 and 34.

In the flexible circuit board inspecting apparatus 10 according to the first embodiment, the first jig 33 can be brought into conductive contact with one surface of the flexible circuit board 11 in the thickness direction of the flexible circuit board 11, and the second jig 34 can be brought into conductive contact with the other surface of the flexible circuit board 11 in the thickness direction. The flexible circuit board 11 can be subjected to the inspection in the state in which the flexible circuit board 11 is sandwiched between the first jig 33 and the second jig 34.

According to this configuration, each of the first jig 33 and the second jig 34 is brought into contact with the longitudinal transport portion 23a at which the straightness of the flexible circuit board 11 is maintained. Therefore, it is possible to conduct an electrical inspection while simultaneously bringing the two jigs 33 and 34 into contact with the accurate positions on both the front and back surfaces of the flexible circuit board 11. Accordingly, it is possible to simultaneously inspect both the surfaces of the flexible circuit board 11. Therefore, it is possible to considerably improve the inspection efficiency.

In the flexible circuit board inspecting apparatus 10 according to the first embodiment, the inspection part mechanism 30 includes the X-Y movement mechanism (the longitudinal feed mechanism 64 and the lateral feed mechanism 67), the Z movement mechanism (the advancement and retreat mechanism 70), and the attitude change mechanism (the rotary mechanism 73). The X-Y movement mechanism is capable of moving the first jig 33 (the second jig 34) within the plane parallel with the flexible circuit board 11. The Z movement mechanism is capable of moving the first jig 33 (the second jig 34) in parallel with the thickness direction of the flexible circuit board 11. The attitude change mechanism is capable of changing the inclination of the first jig 33 (the second jig 34) within the plane parallel with the flexible circuit board 11.

According to this configuration, it is possible to bring and separate each of the jigs 33 and 34 into contact with and from the unit circuit board 12 formed on the flexible circuit board 11 while appropriately bringing each of the jigs 33 and 34 into alignment with the unit circuit board 12. Therefore, it is possible to smoothly conduct an inspection.

In the flexible circuit board inspecting apparatus 10 according to the first embodiment, the inspection part mechanism 30 includes the cameras 91 and 92 for capturing an image of the flexible circuit board 11. The inspection part mechanism 30 brings the jigs 33 and 34 into alignment with the flexible circuit board 11, based on the images of the flexible circuit board 11 captured by the cameras 91 and 92.

According to this configuration, it is possible to bring the jigs 33 and 34 into alignment with the flexible circuit board 11 with high accuracy, based on the actually captured images of the flexible circuit board 11.

In the flexible circuit board inspecting apparatus 10 according to the first embodiment, the inspection part mechanism 30 includes the first jig 33, the second jig 34, the first camera 91, and the second camera 92. The first jig 33 is disposed at one side of the flexible circuit board 11 transported on the longitudinal transport portion 23a, in the thickness direction of the flexible circuit board 11. The second jig 34 is disposed at the other side of the flexible circuit board 11 in the thickness direction. The first camera 91 is disposed at one side of the flexible circuit board 11 in the thickness direction. The second camera 92 is disposed at the other side of the flexible circuit board 11 in the thickness direction. The first camera 91 is capable of capturing an image of the second jig 34. The second camera 92 is capable of capturing an image of the first jig 33.

According to this configuration, the camera 91 (92) captures the image of the jig 34 (33) disposed at the opposite side to the camera 91 (92) in the thickness direction of the flexible circuit board 11 with the flexible circuit board 11 interposed between the camera 91 (92) and the jig 34 (33). Thus, it is possible to obtain useful information concerning a positional relation, a surface state, and the like of the jig 34 (33) and to utilize the information for the purpose of maintenance and the like.

The flexible circuit board inspecting apparatus 10 according to the first embodiment further includes the feed part 21 capable of setting thereon the circuit board roll 11a from which the flexible circuit board 11 is successively fed.

According to this configuration, it is possible to successively feed the flexible circuit board 11 from the circuit board roll 11a and to successively inspect the large number of unit circuit boards 12. Therefore, it is possible to improve the inspection efficiency.

Figure 4:
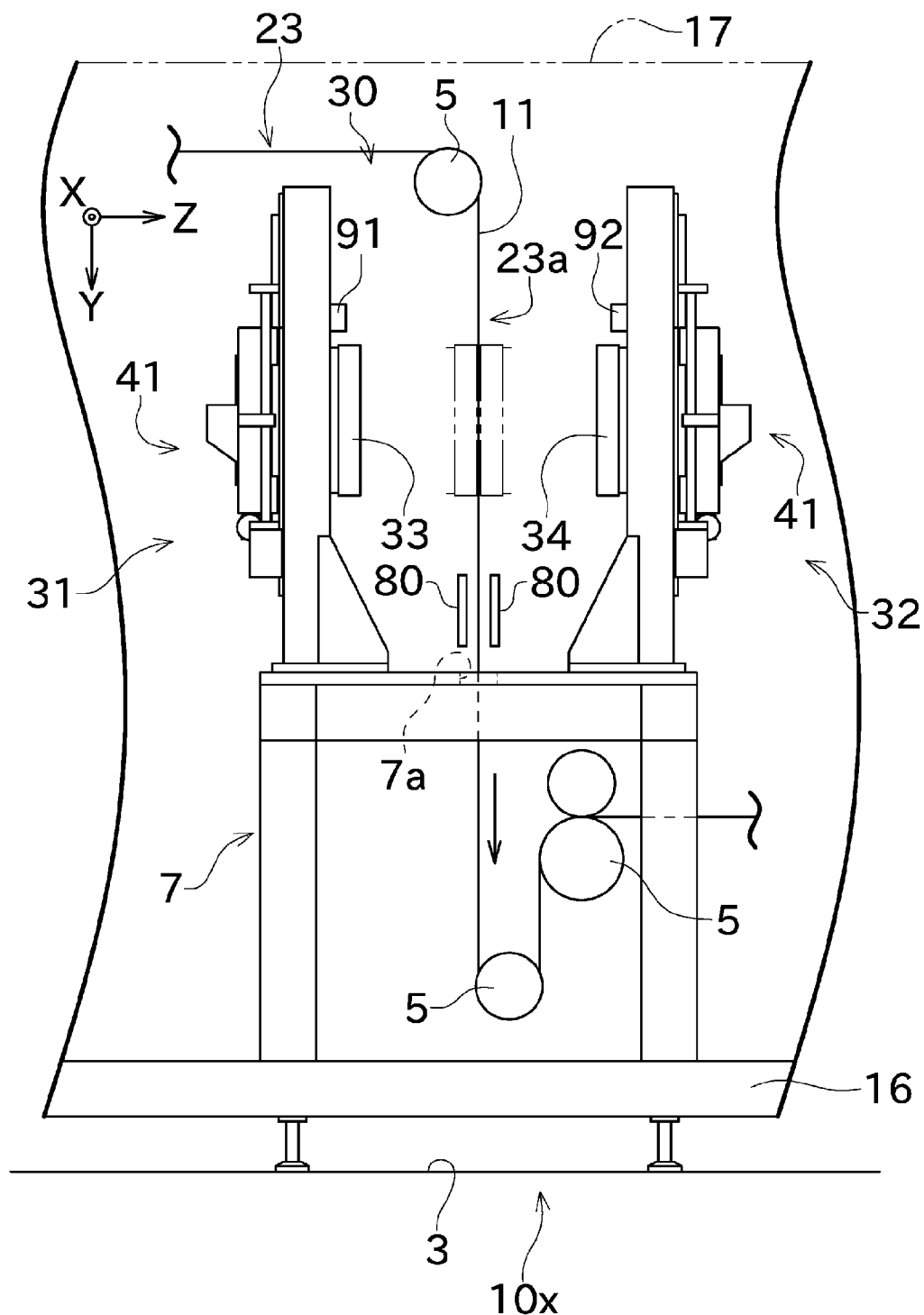
FIG. 4 is a front view illustrating a modification in which the flexible circuit board inspecting apparatus includes an electrostatic suction plate.

Next, a description will be given of a modification of the first embodiment. FIG. 4 is a front view illustrating the modification in which the flexible circuit board inspecting apparatus 10 includes electrostatic suction plates 80 and 80. In the modification of the first embodiment, the identical or similar constituents with or to those described in the first embodiment are denoted with the identical reference signs in FIG. 4; therefore, the description thereof will not be given here.

As illustrated in FIG. 4, a flexible circuit board inspecting apparatus 10x according to the modification of the first embodiment includes the pair of electrostatic suction plates (foreign matter recovery parts) 80 and 80 disposed on an inspection table 7 such that a flexible circuit board 11 on a longitudinal transport portion 23a is sandwiched between the electrostatic suction plates 80 and 80. Each of the electrostatic suction plates 80 and 80 is disposed to be appropriately spaced apart from the flexible circuit board 11. Moreover, the electrostatic suction plates 80 and 80 are disposed at a height lower than a height of jigs 33 and 34.

Each of the electrostatic suction plates 80 and 80 is applied with high pressure to recover by suction a falling foreign matter such as a particle generated, for example, when the jigs 33 and 34 are brought into contact with and separated from the flexible circuit board 11. Thus, it is possible to avoid degradation in quality of the flexible circuit board 11 due to the foreign matter falling and adhering to the flexible circuit board 11.

As described above, the flexible circuit board inspecting apparatus 10x according to the modification of the first embodiment includes the electrostatic suction plates 80 and 80 configured to recover a foreign matter and disposed at the height lower than the height of the jigs 33 and 34 (or a height of locations where the jigs 33 and 34 are brought into contact with the flexible circuit board 11).

According to this configuration, even in a case where a foreign matter such as a particle is generated at the locations where the jigs 33 and 34 are brought into contact with and separated from the flexible circuit board 11, the electrostatic suction plates 80 and 80 can recover the foreign matter falling under its own weight. Therefore, it is possible to avoid degradation in quality of the flexible circuit board 11 due to the adhesion of the foreign matter.

Figure 5:
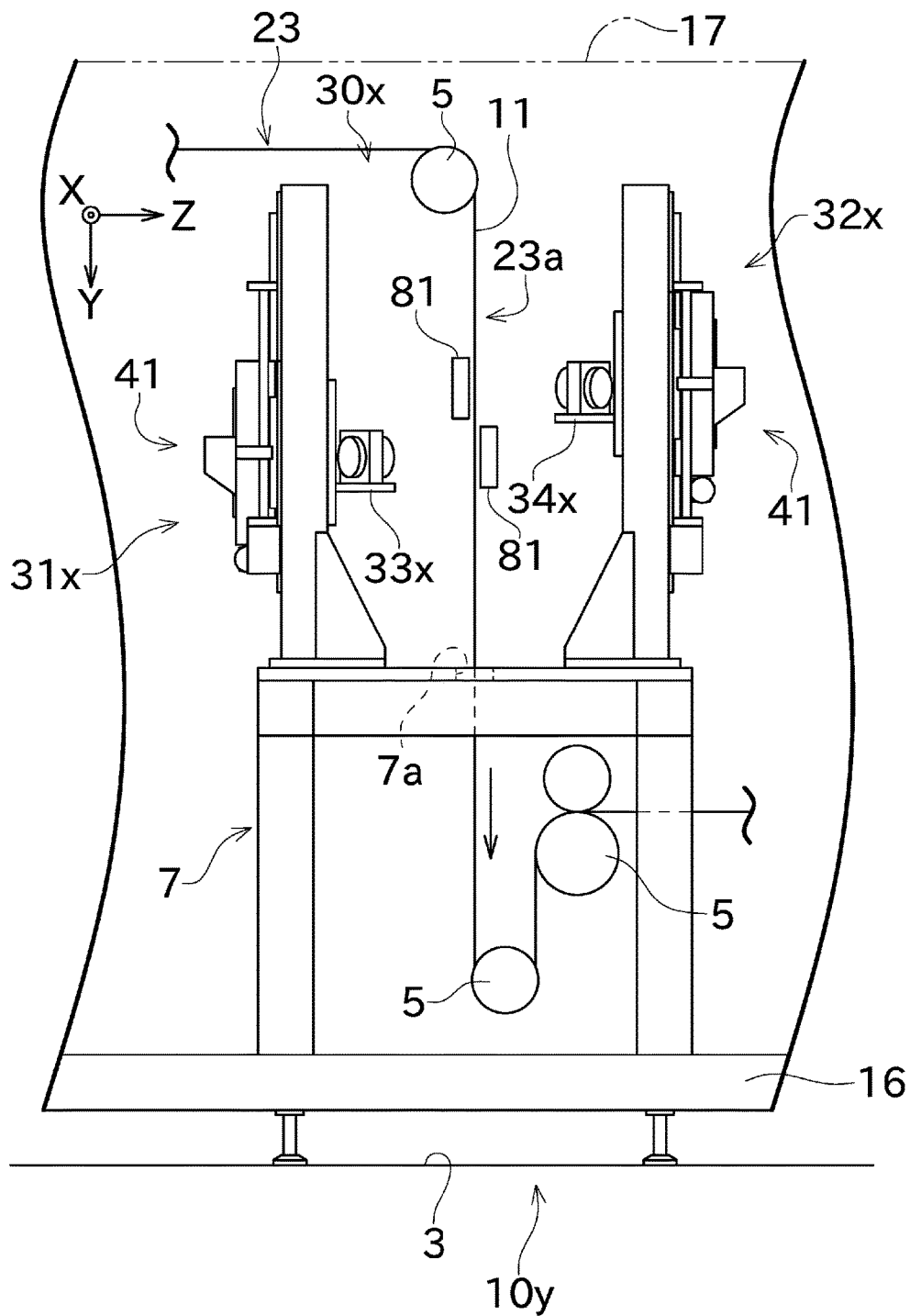
FIG. 5 is a front view illustrating a configuration around a longitudinal transport portion, in a flexible circuit board inspecting apparatus according to a second embodiment.

With reference to FIG. 5, next, a description will be given of a flexible circuit board inspecting apparatus 10y according to a second embodiment. The flexible circuit board inspecting apparatus 10y according to the second embodiment is configured to conduct an optical inspection, rather than an electrical inspection, on a flexible circuit board 11. The flexible circuit board inspecting apparatus 10y includes an inspection part mechanism 30x. The inspection part mechanism 30x includes a first optical unit mechanism 31x and a second optical unit mechanism 32x in place of the first jig mechanism 31 and the second jig mechanism 32 described in the first embodiment.

The first optical unit mechanism 31x includes a first optical unit 33x in place of the first jig 33 of the first jig mechanism 31 described in the first embodiment. Likewise, the second optical unit mechanism 32x includes a second optical unit 34x in place of the second jig 34 of the second jig mechanism 32 described in the first embodiment. In the second embodiment, accordingly, each of the optical units 33x and 34x is equivalent to an inspection part. Each of the two optical unit mechanisms 31x and 32x includes a movement mechanism 41 which is similar in configuration to the movement mechanism 41 described in the first embodiment.

Each of the first optical unit 33x and the second optical unit 34x is configured to optically inspect a flexible circuit board 11. In the second embodiment, each of the optical units 33x and 34x includes an optical device for the optical inspection. Specific examples of the optical device may include, but not limited thereto, a two-dimensional camera, a three-dimensional camera, a lighting device for illumination, a laser irradiator, and the like. Each of the two optical units 33x and 34x is capable of measuring a shape of a predetermined inspection area defined on the flexible circuit board 11 (e.g., a width or height of a protrusion formed on the inspection area).

The movement mechanisms 41 and 41 of the optical unit mechanisms 31x and 32x are capable of moving the two optical units 33x and 34x within an X-Y plane, moving the two optical units 33x and 34x in a Z direction, and changing attitudes of the two optical units 33x and 34x within the X-Y plane. The optical units 33x and 34x move in the Z direction so as to be brought close to and distanced from the flexible circuit board 11. Thus, it is possible to bring a length from the optical units 33x and 34x to the flexible circuit board 11 into agreement with a predetermined inspection length which is suitable for the measurement by the optical device.

The flexible circuit board inspecting apparatus 10y also includes a non-contact holding part 81 disposed at an opposite side to the first optical unit 33x with the flexible circuit board 11 interposed between the non-contact holding part 81 and the first optical unit 33x. The flexible circuit board inspecting apparatus 10y also includes a non-contact holding part 81 disposed at an opposite side to the second optical unit 34x with the flexible circuit board 11 interposed between the non-contact holding part 81 and the second optical unit 34x. Each of the non-contact holding parts 81 and 81 ejects compressed air, thereby holding the flexible circuit board 11 in a non-contact manner, based on, for example, the Bernoulli's principle.

As described above, in the flexible circuit board inspecting apparatus 10y according to the second embodiment, the inspection part mechanism 30x includes, as an inspection part, the optical units 33x and 34x each configured to measure the inspection area on the flexible circuit board 11. The inspection part mechanism 30x brings and distances the optical units 33x and 34x close to and from the flexible circuit board 11 to maintain the inspection length from the optical units 33x and 34x to the flexible circuit board 11.

According to this configuration, it is possible to appropriately control the length from the optical units 33x and 34x to the flexible circuit board 11. Therefore, it is possible to smoothly conduct an optical inspection.

Figure 6:
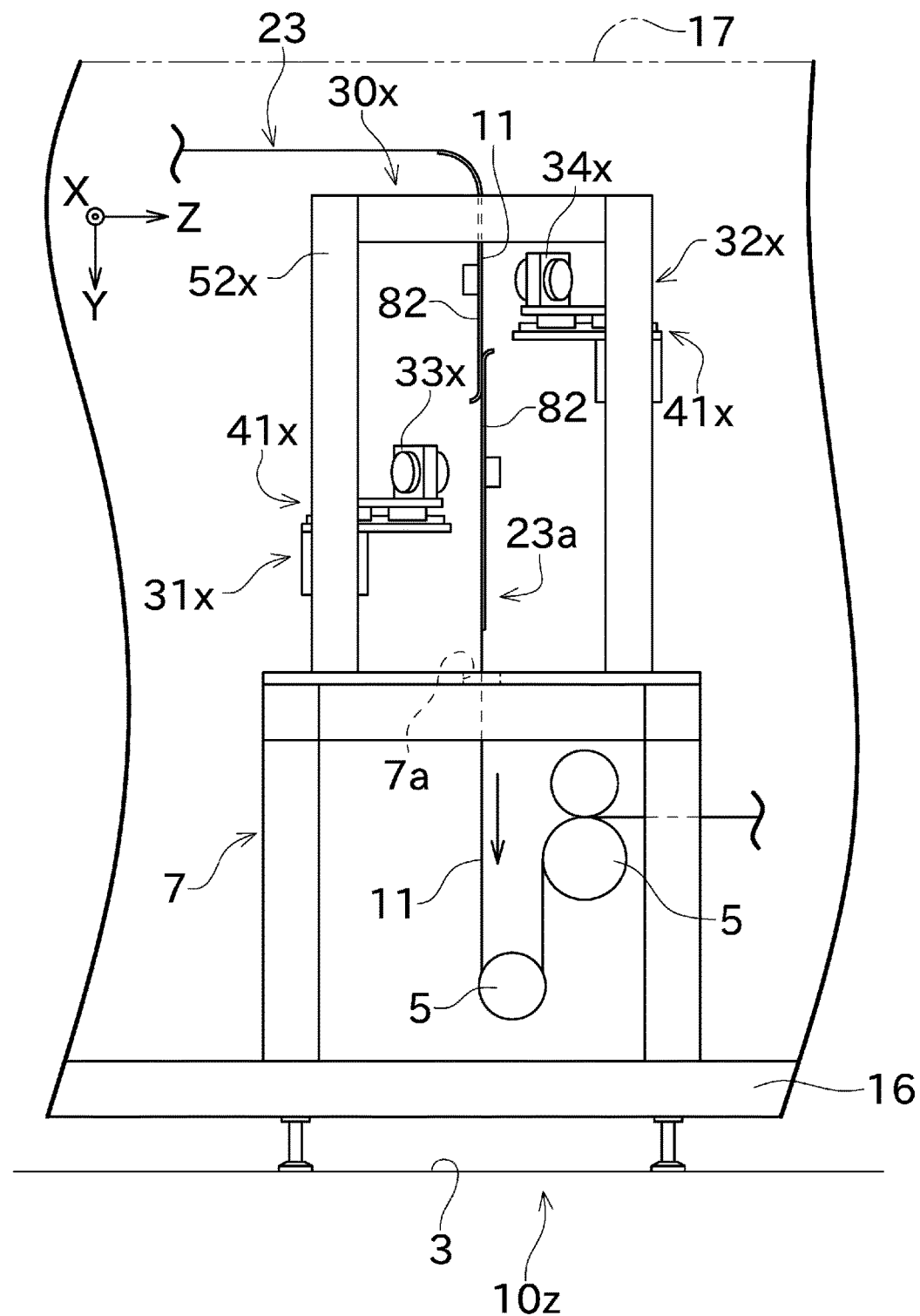
FIG. 6 is a front view illustrating a modification of the second embodiment.

With reference to FIG. 6, next, a description will be given of a flexible circuit board inspecting apparatus 10z according to a modification of the second embodiment. In the flexible circuit board inspecting apparatus 10z, movement mechanisms 41x and 41x of optical unit mechanisms 31x and 32x include feed mechanisms for moving optical units 33x and 34x in an X direction and a Z direction. Each of the feed mechanisms may be formed of a screw feed mechanism which is similar to that of the movement mechanism 41 described above. In the modification of the second embodiment, the optical units 33x and 34x are not capable of moving in a Y direction (a vertical direction).

Each of the optical units 33x and 34x is attached to a fixed frame 52x formed of a frame-shaped member and mounted on an inspection table 7. The optical units 33x and 34x are disposed at different heights from each other. Therefore, it is possible to avoid such a problem that illumination for use in an image capturing operation of one of the optical units 33x and 34x exerts an influence on an image capturing operation of the other one of the optical units 33x and 34x.

The flexible circuit board inspecting apparatus 10z includes a suction guide 82 disposed at an opposite side to the first optical unit 33x with a flexible circuit board 11 interposed between the suction guide 82 and the first optical unit 33x. Moreover, the flexible circuit board inspecting apparatus 10z also includes a suction guide 82 disposed at an opposite side to the second optical unit 34x with the flexible circuit board 11 interposed between the suction guide 82 and the second optical unit 34x. Each of the suction guides 82 and 82 is formed into a wide flat plate shape, and has a suction port (not illustrated) connected to an appropriate negative pressure source. Thus, upon inspection by an inspection part mechanism 30, the suction guide 82 is capable of holding the flexible circuit board 11 by suction.

As described above, in the flexible circuit board inspecting apparatus 10z according to the modification of the second embodiment, the inspection part mechanism 30x includes, as an inspection part, the first optical unit 33x configured to measure an inspection area on one surface of the flexible circuit board 11 in a thickness direction of the flexible circuit board 11, and the second optical unit 34x configured to measure an inspection area on the other surface of the flexible circuit board 11 in the thickness direction. The first optical unit 33x and the second optical unit 34x are disposed at different heights from each other.

According to this configuration, it is possible to simultaneously inspect both the front and back surfaces of the flexible circuit board 11. Therefore, it is possible to improve the efficiency of an optical inspection. Moreover, the two optical units 33x and 34x are disposed at different heights from each other. Therefore, it is possible to realize such a layout that the two optical units 33x and 34x are less prone to have a mutual influence upon measurement of the inspection areas.

The flexible circuit board inspecting apparatus 10z according to the modification of the second embodiment includes the suction guides 82 and 82 configured to suck the flexible circuit board 11 by negative pressure and disposed on a longitudinal transport portion 23a.

According to this configuration, the suction guide 82 can fixedly hold the flexible circuit board 11 oriented in the vertical direction. Therefore, it is possible to smoothly conduct an inspection using the inspection part mechanism 30x. Moreover, it is possible to easily switch between the hold and release of the flexible circuit board 11 by switching between the start and stop of the supply of the negative pressure to the suction guide 82.

The foregoing description concerns an exemplary embodiment of the disclosure and a modification of the embodiment. The configurations described above may be changed as follows.

In an illustrative embodiment, the flexible circuit board 11 is transported in the downward vertical direction on the longitudinal transport portion 23a. Alternatively, the flexible circuit board 11 may be transported in an upward vertical direction. Depending on an inspection process, moreover, the flexible circuit board 11 is not transported only in a forward direction, but may be temporarily transported in a reverse direction (reverse transport). Further, the transport path 23 may be substantially configured with the longitudinal transport portion 23a in such a manner that the feed part 21 and the reel part 22 are disposed above and below the longitudinal transport portion 23a, respectively.

The arrangement of the unit circuit boards 12 on the flexible circuit board 11 is not limited to that illustrated in FIG. 3, but may be optionally changed in accordance with circumstances. For example, at least three unit circuit boards 12 may be arranged in the widthwise direction of the flexible circuit board 11.

In an illustrative embodiment, the jigs 33 and 34 are configured to come into contact with an inspection point on a circuit pattern of one unit circuit board. Alternatively, the jigs 33 and 34 may be configured to simultaneously come into contact with inspection points on circuit patterns of at least two unit circuit boards. In FIG. 3, for example, two unit circuit boards 12 are arranged in the widthwise direction of the flexible circuit board 11. The jigs 33 and 34 may be configured to simultaneously come into contact with the inspection points on the circuit patterns of the two unit circuit boards 12 and 12. In this case, it is possible to simultaneously inspect two unit circuit boards. Moreover, there is no necessity to move the jigs 33 and 34 so much in the widthwise direction (the X direction) of the flexible circuit board 11. Therefore, it is possible to considerably improve the inspection efficiency. As described above, the jigs 33 and 34 are detachable to the mounting plate 74. Therefore, it is possible to easily replace the jigs 33 and 34 in accordance with the specification of a flexible circuit board 11 to be inspected.

In the modification of the first embodiment illustrated in FIG. 4, a receiving member configured to receive a foreign matter falling by gravity may be provided as the foreign matter recovery part, in place of or in addition to the electrostatic suction plate 80.

The foregoing disclosure has been specifically described and illustrated in connection with certain illustrative embodiments. However, it is clearly understood that the embodiments are by way of illustration and example only and are not to be taken by way of limitation. The spirit and scope of the invention are limited only by the terms of the appended claims.

What is claimed is:

1. A flexible circuit board inspecting apparatus comprising:
    a transport path configured to successively transport a flexible circuit board comprising a plurality of unit circuit boards; and
    an inspection part mechanism configured to selectively position an inspection part relative to the transport path for inspecting the flexible circuit board,
    wherein
    the flexible circuit board has major surfaces separated by a thickness of the flexible circuit board,
    the thickness of the flexible circuit board has a direction associated therewith,
    the transport path includes a transport portion configured to
        transport the flexible circuit board substantially perpendicular to the thickness direction of the flexible circuit board and substantially along the transport path in at least one of an upward direction opposing gravity or a downward direction assisted by gravity and
        transport the flexible circuit board substantially parallel to the major surfaces, and
    said positioning by the inspection part mechanism includes bringing the inspection part to the flexible circuit board transported on the transport portion.

2. The flexible circuit board inspecting apparatus of claim 1, wherein
    the inspection part mechanism comprises the inspection part, the inspection part comprising a jig having a plurality of probes configured to move into conductive contact with the flexible circuit board, and
    said positioning by the inspection part mechanism includes selectively bringing the inspection part and the flexible circuit board into contact with each other and separating the inspection part from the flexible circuit board.

3. The flexible circuit board inspecting apparatus of claim 2, wherein
    the jig includes a first jig configured to move into conductive contact with a first major surface of the flexible circuit board, and a second jig configured to move into conductive contact with a second major surface of the flexible circuit board, the first and second major surfaces separated in the thickness direction, and
    the inspection part is configured to inspect the flexible circuit board in a state in which the flexible circuit board is in conductive contact with the first jig and the second jig.

4. The flexible circuit board inspecting apparatus of claim 3, wherein
    the first jig and the second jig are configured to sandwich the flexible circuit board therebetween when in conductive contact therewith.

5. The flexible circuit board inspecting apparatus of claim 3, wherein
    the inspection part mechanism includes
    a first movement mechanism configured to move at least one of the first jig and the second jig within a plane parallel with the flexible circuit board,
    a second movement mechanism configured to move at least one of the first jig and the second jig in the thickness direction, and
    an attitude change mechanism configured to change the inclination of at least one of the first jig and the second jig within the plane parallel with the flexible circuit board.

6. The flexible circuit board inspecting apparatus of claim 5, wherein
    said inclination is an in-plane rotation of said first jig and/or said second jig.

7. The flexible circuit board inspecting apparatus of claim 1, wherein
    the inspection part mechanism comprises the inspection part, the inspection part comprising an optical unit configured to measure an inspection area on the flexible circuit board, and
    said positioning by the inspection part mechanism includes selectively moving the inspection part close to and away from the flexible circuit board to maintain an inspection distance from the inspection part to the flexible circuit board.

8. The flexible circuit board inspecting apparatus of claim 7, wherein
    the optical unit comprises a first optical unit configured to measure an inspection area on a first major surface of the flexible circuit board, and a second optical unit configured to measure an inspection area on a second major surface of the flexible circuit board, the first and second major surfaces separated in the thickness direction, and the first optical unit and the second optical unit are disposed at different vertical positions relative to each other.

9. The flexible circuit board inspecting apparatus of claim 1,
wherein
the inspection part mechanism comprises an image capturing part configured to capture an image of the flexible circuit board, and
the inspection part mechanism is configured to bring the inspection part into alignment with the flexible circuit board, based on captured image information obtained by capturing the image of the flexible circuit board by the image capturing part.

10. The flexible circuit board inspecting apparatus of claim 9,
wherein
the inspection part mechanism further comprises
a first inspection part disposed at a first side of the flexible circuit board transported on the transport portion,
a second inspection part disposed at a second side of the flexible circuit board,
a first image capturing part disposed at the first side of the flexible circuit board, and
a second image capturing part disposed at the second side of the flexible circuit board,
the first image capturing part configured to capture an image of the second inspection part, and
the second image capturing part configured to capture an image of the first inspection part.

11. The flexible circuit board inspecting apparatus of claim 1, further comprising:
a supply part configured to set thereon a circuit board roll from which the flexible circuit board is successively supplied.

12. The flexible circuit board inspecting apparatus of claim 1, further comprising:
a foreign matter recovery part configured to recover foreign matter, the foreign matter recovery part being disposed at a height vertically below a height of the inspection part.

13. The flexible circuit board inspecting apparatus of claim 1, further comprising:
a suction guide configured to suck the flexible circuit board by negative pressure, the suction guide being disposed on the transport portion.

14. A flexible circuit board inspecting apparatus comprising:
a transport path configured to successively transport a plurality of flexible unit circuit boards arranged in a flexible circuit board roll to a vertically oriented portion of said transport path for inspection, and
an inspection part mechanism comprising at least one inspection part configured to inspect at least one of the plurality of flexible unit circuit boards, the inspection part mechanism being configured to selectively position, at said vertically oriented position, at least one of the at least one inspection part toward the at least one flexible unit circuit board and/or away from the at least one flexible unit circuit board,
wherein each of said flexible unit circuit boards have a first major surface and a second major surface separated by a thickness having a direction associated therewith, and
the transport path is configured to
transport said circuit boards substantially perpendicular to the thickness direction of the flexible circuit board and substantially along the transport path, in at least one of an upward direction opposing gravity or a downward direction assisted by gravity and
transport said circuit board substantially parallel to the first major surface and the second major surface in said vertically oriented portion.

15. The flexible circuit board inspecting apparatus of claim 14 wherein the transport path is configured to successively transport at least a portion of said circuit board roll to the vertically oriented portion of the transport path such that said portion of said circuit board roll is suspended from a position vertically above at least one flexible unit circuit board to be inspected.

16. The flexible circuit board inspecting apparatus of claim 15 wherein the transport path is configured to transport said suspended portion of the circuit board roll such that said suspended portion of the circuit board roll is held substantially planar by gravity.

17. The flexible circuit board inspection apparatus of claim 16,
wherein
the inspection part comprises a jig having a plurality of probes configured to move into conductive contact with the flexible unit circuit board to be inspected, and
said positioning by the inspection part mechanism includes selectively bringing the inspection part and the flexible unit circuit board to be inspected into contact with each other and separating the inspection part from the flexible unit circuit board to be inspected.

18. The flexible circuit board inspection apparatus of claim 17,
wherein
the jig includes a first jig configured to move into conductive contact with the first major surface of the flexible unit circuit board to be inspected, and a second jig configured to move into conductive contact with the second major surface of the flexible unit circuit board to be inspected, and
the first jig and the second jig are configured to sandwich the flexible unit circuit board to be inspected therebetween.

19. The flexible circuit board inspection apparatus of claim 16,
wherein
the inspection part comprises an optical unit configured to measure an inspection area on the flexible circuit board, and
said positioning by the inspection part mechanism includes selectively moving the inspection part close to and away from the flexible unit circuit board to be inspected to maintain an inspection distance from the inspection part to the flexible unit circuit board to be inspected.

20. The flexible circuit board inspection apparatus of claim 19,
wherein
the optical unit comprises a first optical unit configured to measure an inspection area on the first major surface of the flexible unit circuit board to be inspected and a second optical unit configured to measure an inspection area on the second major surface of the flexible unit circuit board to be inspected, and the first optical unit and the second optical unit are disposed at different vertical positions relative to each other.

* * * * *